US008841300B2

(12) United States Patent
Held

(10) Patent No.: US 8,841,300 B2
(45) Date of Patent: Sep. 23, 2014

(54) TREATMENT FOR PARKINSON'S DISEASE—COMBINATION HIGH DOSE SEROTONERGIC SYNAPTIC REUPTAKE INHIBITOR WITH PHOSPHODIESTERASE INHIBITOR

(75) Inventor: Jerry M. Held, Cottonwood, AZ (US)

(73) Assignee: Jerry M. Held, San Diego, CA (US)

( * ) Notice: Subject to any disclaimer, the term of this patent is extended or adjusted under 35 U.S.C. 154(b) by 864 days.

(21) Appl. No.: 11/542,010

(22) Filed: Oct. 2, 2006

(65) Prior Publication Data

US 2008/0081806 A1  Apr. 3, 2008

(51) Int. Cl.
| | | |
|---|---|---|
| *A01N 43/58* | (2006.01) |
| *A01N 43/60* | (2006.01) |
| *A61K 31/50* | (2006.01) |
| *A61K 31/495* | (2006.01) |
| *A61K 31/497* | (2006.01) |
| *A01N 43/90* | (2006.01) |
| *A61K 31/519* | (2006.01) |
| *A01N 33/24* | (2006.01) |
| *A61K 31/15* | (2006.01) |
| *A01N 33/02* | (2006.01) |
| *A61K 31/135* | (2006.01) |
| *A61K 31/137* | (2006.01) |
| *A61K 45/06* | (2006.01) |
| *A61K 31/551* | (2006.01) |

(52) U.S. Cl.
CPC .............. *A61K 45/06* (2013.01); *A61K 31/137* (2013.01); *A61K 31/551* (2013.01); *A61K 31/519* (2013.01)
USPC .................. 514/250; 514/252.12; 514/253.02; 514/262.1; 514/640; 514/646

(58) Field of Classification Search
USPC ............ 514/250, 252.12, 253.02, 262.1, 640, 514/646
See application file for complete search history.

(56) References Cited

U.S. PATENT DOCUMENTS

| | | | | |
|---|---|---|---|---|
| 5,962,463 | A * | 10/1999 | Nitsch et al. .................. 514/284 |
| 2004/0067957 | A1 | 4/2004 | Jerussi et al. |
| 2005/0009835 | A1 | 1/2005 | Thomas |
| 2006/0235005 | A1 | 10/2006 | Goff |
| 2008/0081806 | A1 | 4/2008 | Held |
| 2008/0188480 | A1 * | 8/2008 | Black ............................ 514/250 |
| 2009/0062313 | A1 * | 3/2009 | Kass et al. ................. 514/262.1 |

FOREIGN PATENT DOCUMENTS

| | | |
|---|---|---|
| FR | 2810886 A1 | 1/2002 |
| WO | WO 01/78711 A2 | 10/2001 |
| WO | WO 02/089808 A1 | 11/2002 |
| WO | WO 03/028730 A2 | 4/2003 |
| WO | WO 03/056899 A2 | 7/2003 |
| WO | WO 2005/089766 A1 * | 9/2005 |
| WO | WO 2006/001877 A2 | 1/2006 |
| WO | WO 2006/016262 A1 | 2/2006 |
| WO | WO 2006/091542 A2 | 8/2006 |

OTHER PUBLICATIONS

Caley et al. 'Extrapyramidal reactions and the selective serotonin-reuptake inhibitors', Ann Pharmacother, 31(12):1-9 (1997).
Gibbons et al. 'Microglia induce neural cell death via a proximity-dependent mechanism involving nitric oxide', Brain Res., 1084(1):1-15 (2006).
Hoffpauir et al. 'Nitric oxide transiently converts synaptic inhibition to excitation in retinal amacrine cells', J. Neurophysiol., 95(5):2866-77 (2006).
Chateau (2007), In Vitro Reconstruction of Neuro-Epidermal Connections, Investigative Dermatology, 127:4.
G. Burke et al.: "Clinical Neurosciences 2005 Meeting, Torquay, England, Sep. 7 9, 2005/ Effekt of sildenafil citrate (Viagra) on cerebral blood flow in patients with multiple sclerosis" Journal of Neurology Neurosurgery & Psychiatry, vol. 77, No. 1, Jan. 2006, p. 130.
International Search Report from PCT/US2008/006467, dated Dec. 29, 2008.
IPRP (WO) from PCT/US2008/006467, dated Nov. 24, 2009.
Kassis et al. (1977), "Synthesis of Prostaglandins in Psoriatic Skin", Archives of Dermatological Research, 259:207-212.
Lysketos et al. "Treating Depression in Alzheimer Disease", Arch. Gen. Psychiatry 60:737-746 (2003).
Misery (1997), "Skin, immunity and the nervous system", British Journal of Dermatology, 137(6):845-850.
Munro et al. "Cognitive Response to Pharmacological Treatment for Depression in Alzheimer Disease", Am. J. Geriatr. Psychiatry 12(5): 491-98 (2004).

(Continued)

*Primary Examiner* — Kara R McMillian
(74) *Attorney, Agent, or Firm* — Lathrop & Gage LLP

(57) ABSTRACT

A new treatment methodology and pharmacological composition for the treatment and remission of Parkinson's Disease and other neurological diseases are provided. The medication and treatment are based on the use of a combination of a phosphodiesterase inhibitor medication, commonly used to treat male erectile dysfunction, and a high-dose of serotonergic synaptic reuptake inhibitor medication, commonly used to treat depression, anxiety disorders, obsessive compulsive disorder and various panic phobias. The treatment regime is based upon the discovery that the primary cause of PD and various other related neurological conditions is dysfunction in the serotonergic pathways involving the brainstem, nucleus of Raphe, and various projecting serotonergic fibers. It has been determined that this dysfunction can be overcome by increasing the levels of the ligands and neurotransmitters cyclic-GMP and serotonin and the consequential increased binding of these ligands and neurotransmitters to efferent neuron receptors in the synapse. Testing indicates that the inventive treatment changes Parkinson's Disease from a debilitating, progressive, frightening, and previously untreatable pre-morbid condition to one that is rapidly reversible.

8 Claims, 1 Drawing Sheet

(56) References Cited

OTHER PUBLICATIONS

Patel, "Pharmacotherapy of Cognitive Impairment in Alheinmer's Disease: A Review", Journal of Geriatric Psychiatry and Neurology, 8:81-95 (1995).

Petracca et al. "A Double-Blind, Placebo-Controlled Study of Fluoxetine with Depressed Patients With Alzheimer's Disease", International Psychogeriatrics, 13(2): 233-40 (2001).

Salonia A et al: "A Prospective Study Comparing Paroxetine Alone Versus Paroxetine Plus Sildenafil in Patients With Premature Ejaculation" Journal of Urology, Baltimore, MD, US, vol. 168, No. 6, Dec. 1, 2002, pp. 2486-2489.

Sancero (2006), "Role of Neuropeptides in Psoriasis", British Journal of Dermatology, 155(5):876-882.

Swope D M: "Preliminary Report: Use of Sildenafil to Treat Dyskinesias in Patients With Parkinson's Disease" Neurology,Lippincott Williams & Wilkins, Philadelphia, US, vol. 54, No. 7, Apr. 11, 2000, p. A90.

Uthayathas Subramaniam et al: "Versatile effects of sildenafil: recent pharmacological applications." Pharmacological Reports, vol. 59, No. 2, Mar. 2007, pp. 150-163.

\* cited by examiner

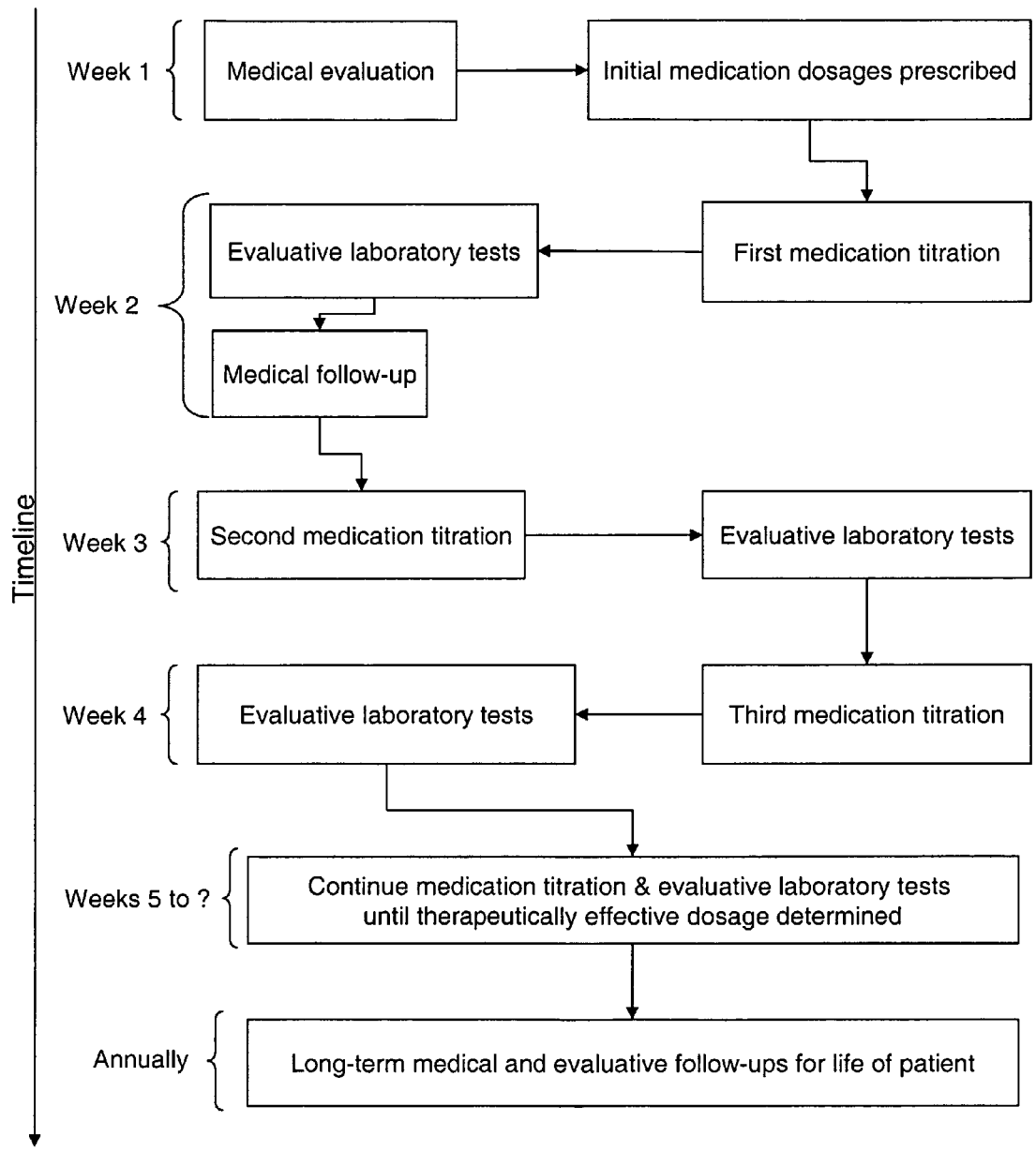

TREATMENT FOR PARKINSON'S DISEASE—COMBINATION HIGH DOSE SEROTONERGIC SYNAPTIC REUPTAKE INHIBITOR WITH PHOSPHODIESTERASE INHIBITOR

FIELD OF THE INVENTION

The current invention is directed to a methodology and pharmaceutical combination for treating neurological disorders, and more specifically to a method and composition including the administration of a combination of a serotonergic synaptic reuptake inhibitor and a phosphodiesterase inhibitor.

BACKGROUND OF THE INVENTION

Parkinson's Disease is a devastating neurological illness. It is currently estimated to affect over thirty million people worldwide and its prevalence is increasing at an alarming rate as the population ages.

Parkinson's Disease (PD) is characterized by progressive debilitating somatic symptoms including, tremors, rigidity, bradykinesis, and postural problems. PD patients also commonly experience dementia, ataxia and dysphasia, as well as secondary depression, psychosis and emotional suffering. Perhaps most troubling, the average life expectancy of patients with PD is substantially reduced. As a result, there is a high emotional cost to the families of PD patients, and the financial burden both to the patients and to the health care system is astronomical.

Partly due to the rising profile of the disease, tremendous efforts have been made over the past four decades in an attempt to find an effective treatment or cure for PD. Unfortunately, despite these efforts most patients have experienced little relief from current treatment regimes, including from available medications, surgeries and implants. Indeed, the benefits from the standard treatments are slight, usually short lived, and often are accompanied by appreciable toxicity and expense. Finally, although promising, further testing and use of stem cells or other embryonic cells appears to lie far in the future.

Accordingly, a need exists for a new methodology for treating PD and other neurological disorders that is currently available, affordable, and relatively free of side-effects and contraindications.

SUMMARY OF THE INVENTION

The presented invention is directed to a novel methodology and pharmaceutical combination for the treatment of neurological disease such as PD, by administering a combination of a serotonergic synaptic reuptake inhibitor (SSRI) and a phosphodiesterase inhibitor (PI).

In one embodiment of the invention, any suitable SSRI medication may be used, including, for example Luvox, Prozac, Zoloft, and Paxil.

In another embodiment of the invention, any PI medication suitable for increasing cyclic GMP levels in the synaptic clefts of neurons may be used, including, for example Cialis, and Viagra.

In yet another embodiment of the invention, the medications of the treatment are administered individually.

In still another embodiment of the invention, the medications of the treatment are provided in a suitable combined form, such as, for example, in a once-weekly or monthly patch, long-term injection, combined pill, or implant.

In still yet another embodiment of the invention, the treatment regime includes regular monitoring of relevant physiological functions, including, for example, blood tests for liver function, kidneys, and electrolytes, and/or physical exams, including EKG and treadmill tests.

In still yet another embodiment of the invention, the method and composition are designed to treat a neurological disorder. In such an embodiment, the disorder may be any one of the following: Alzheimer's Disease, Multiple Sclerosis, Amyotrophic Lateral Sclerosis, Progressive Supranuclear Palsy, Tardive Dyskinesia, Essential Dyskensia, Hereditary Hyperkinesis, restless leg syndrome and sleep apnea

BRIEF DESCRIPTION OF THE SEVERAL VIEWS OF THE DRAWINGS

These and other features and advantages of the present invention will be better understood by reference to the following detailed description when considered in conjunction with the accompanying drawings wherein:

FIG. 1 provides an exemplary time line flowchart for administering and monitoring the use of the treatment of the current invention.

DETAILED DESCRIPTION OF THE INVENTION

The current invention is directed to a new method and composition for the treatment of neurological disorders, such as, for example, Parkinson's Disease (PD), involving the administration of a combination of a serotonergic synaptic reuptake inhibitor (SSRI) and a phosphodiesterase inhibitor (PI).

Current medical doctrine posits that PD is caused by defects in the human brain, and specifically by defects in the anatomical areas of the basal ganglia, substantia nigra, nigrostriatal pathways and subthalamic nucleus. Moreover, it is believed that the dopaminergic pathways of the nerve synapses in these defective areas of the brain are the key culprits in PD. Indeed, to the inventor's knowledge all currently available treatment regimes derive from this basic understanding of the disease. However, despite the significant interest in PD, most of these fundamental conclusions are based on inconclusive autopsy findings and toxin effects.

The inventor has reexamined this foundational understanding of PD, and surprisingly discovered a new physiological origin for the disease. In short, the treatment regime of the current invention is based on the discovery that the key areas involved in PD are the Nuclei of Raphe in the brain stem and their various projecting serotonergic fibers. Under this new model of PD, the gross morphological defects observed by past researchers in the substantia nigra, etc. of PD patients can be understood as symptoms or secondary effects caused by denervation or decreased neural tone from the underlying defects in the Nuclei of Raphe. Although not to be bound by theory, it is believed that the underlying defect in the Nuclei of Raphe in patient's suffering from Parkinson's Disease results from a membrane bound protein receptor for the neurotransmitter serotonin and for cyclic GMP. This defect, whether based on hereditary or acquired over time, alters the binding affinity of serotonin and c-GMP, therefore reducing their ability to induce membrane activation of efferent neuron dendritic cytoplasmic changes and ultimately efferent nerve sequence activation. Although the activation would be universal in patient's suffering from neurological disorders such as PD, different efferent neurons, or even components of individual efferent neuron receptor membranes, may contain different concentrations or sensitivities structurally to this activation.

For additional information on the mechanisms of the SSRI and PI compounds of the current invention, and their physiological effect see: 'Nitric oxide transiently converts synaptic inhibition to excitation in retinal amacrine cells, 'J. Neurophysiol., 95(5):2866-77 (2006); 'Microglia induce neural cell death via a proximity-dependent mechanism involving nitric oxide', Brain Res., 1084(1):1-15 (2006); and 'Extrapyramidal reactions and the selective serotonin-reuptake inhibitors', Ann Pharmacother, 31(12):1-9 (1997), the disclosures of which are incorporated herein by reference.

Although the above discussion has focused on one potential mechanism of action for the inventive combination, the invention itself is directed to a pharmaceutical composition and treatment regime consisting of the administration of two medications, one to increase the synaptic concentration of serotonin and the other to increase the synaptic concentration of cyclic GMP. It has been surprisingly shown that increasing the concentrations of these two small molecules will in turn increase binding to the altered, defective membrane protein receptor, countering the decreased affinity.

Any medication suitable for increasing the synaptic concentrations of serotonin and cyclic GMP may be used in the current invention, including currently available medications. Suitable SSRI medications include any drug that provides essentially pure increases in serotonin levels by preventing reuptake into the afferent neuronal axon of this monoamine, such as, for example, Luvox, Prozac, Zoloft, Paxil., etc. Other drugs, such as that affect other neurotransmitters or even combinations of other neurotransmitters may also be used, such as, for example, Cymbalta.

Likewise, any medication suitable for increasing cyclic GMP levels in the synaptic clefts of neurons may be used in the current invention. Suitable cycling GMP medications include any drug that increases the levels of nitric oxide (NO) in the synapse, such as, for example, phosphodiesterase inhibitors. Examples of currently available PI medications include Cialis, Viagra, etc. In such an embodiment, the increased NO levels activate Guanylate Cyclase, a soluble enzyme in the synapse that forms cyclic-GMP, thereby increasing c-GMP levels.

Therapeutic levels of the two combined drugs will vary from individual to individual. For this reason, and to minimize side effects, treatment should begin with individual, rather than combined, SSRI and PI medications. The combination of SSRI and PI medications in patients with Parkinson's Disease in the appropriate amounts and intervals will necessarily be monitored both clinically and chemically by the family practitioner, internist or neurologist as discussed in further detail below. Once therapeutic doses are determined, a combined form as in a once-weekly or monthly patch, long-term injection, combined pill or even implant can be prescribed to provide more stable drug levels throughout the day.

Doses should begin at low levels and be titrated up individually every three days at follow-up visits with the M.D. To ensure maximum patient safety, monitoring should include blood tests for liver and kidney function, as well as electrolyte levels as is the current standard of care when administering the individual drugs. In addition, thorough physical exams, including EKG and probable treadmill tests, should be performed prior to starting treatment. FIG. 1 provides a flowchart of the proposed methodology.

Regardless of the actual dosage regime chosen, the therapeutically effective level should be that which does not cause significant side effects, but minimizes symptoms of the neurological disorder, in this example PD. In the context of the current treatment regime, this level should not be chosen at the dosage level at which improvement begins, but that at which improvement peaks and is maximized. This dosage may change over time, but should mainly reflect changes in the patient's physical state, including, for example, volume of distribution, renal and liver function, weight, etc.

Example 1

Typical Dosage Regime for Medication

The following example dosage experiment was conducted on a 57 year old male PD patient weighing 210 lbs and with a body mass index (b.m.i.) of 0.20. Initial tests were run for kidney function and liver function. The kidney function tests showed a creatinine level of 1.0, and a liver function test (LFT). both of which were within normal limits. The patient was administered with a combination of Cialis and Luvox. Table 1, below provides a summary of the titration regime used to determine the therapeutically effective amount of each drug for this patient. As discussed previously, therapeutically effective amounts are defined as the level of medication required to observe maximum improvement in PD symptoms.

TABLE 1

Exemplary Dosage Regime

| Week | Cialis (mg/frequency) | Luvox (mg/frequency) |
|---|---|---|
| 1 | 5 mg/morning | 12.5 mg/twice daily |
| 1 | 5 mg/morning | 25 mg/twice daily |
| 2 | 5 mg/morning | 50 mg/twice daily |
| 2 | 5 mg/morning | 75 mg/twice daily |
| 3 | 5 mg/morning | 100 mg/twice daily |
| 3 | 5 mg/morning | 150 mg/twice daily |
| 4 | 10 mg/morning | 150 mg/twice daily |
| 4 | 10 mg/twice daily | 150 mg/twice daily |

Although relatively conservative doses are set forth in Table 1, the current invention contemplates the combined use of high-dose SSRI medications, which may be given at doses at our near the upper limit of the approved dose currently used for treating depression, obsessive-compulsive disorder, agoraphobia, etc., with high-dose phosphodiesterase inhibitor medications, which may be given at doses at or near the upper limit of the approved dose currently used to treat male erectile dysfunction or possibly at even higher concentrations such as those approaching the doses conventionally used in treating pulmonary hypertension. Moreover, although the above provides effective doses with the selected medications, it should be understood that one of ordinary skill in that art should be able to establish comparable doses with other combinations of existing and future SSRI and PI medications using similar titration techniques. It should also be understood that the doses, frequencies and other clinical variables of administration and monitoring set forth in the above example were established for the treatment of PD. These variables will also vary with the particular neurological disease or diseases being treated. As clinical use proceeds, other diseases will likely be discovered that are effectively treated by the invention.'

Although the above discussion has focused on the use of the inventive treatment methodology for PD, the method may be used to replace any of the currently existing dopaminergic, etc. medication regimes. In addition, given the similarities in disease mechanism, the invention should be useful in treating dyskinesias, dementias, ataxias, supra-bulbar palsies, including Alzheimer's Disease, Multiple Sclerosis, Amyotrophic Lateral Sclerosis, Progressive Supranuclear Palsy, Tardive Dyskinesia, Essential Dyskensia, Hereditary Hyperkinesis, restless leg syndrome and sleep apnea, etc.

Although specific embodiments are disclosed herein, it is expected that persons skilled in the art can and will design alternative treatment regimes that are within the scope of the following claims either literally or under the Doctrine of Equivalents based on the descriptions found herein. This is particularly likely to occur as this novel treatment methodology and pharmaceutical combination is adopted for widespread use and becomes state of the art in treatment of Parkinson's disease and other neurological diseases. Accordingly, specific additional uses may follow, as experimentation continues on a clinical, hospital, animal model, and microscopic and molecular level.

What I claim as my invention is:

1. A method for the treatment of dementia associated with Alzheimer's disease comprising administering a therapeutically effective amount of fluvoxamine and a therapeutically effective amount of tadalafil or sildenafil to a patient diagnosed with Alzheimer's disease.

2. The method of claim 1, wherein the fluvoxamine and tadalafil are administered in a pharmaceutically acceptable form selected from the group consisting of two separate pills, a patch, an injection, a combined pill, and an implant.

3. The method of claim 1, wherein the therapeutically effective amount is the dosage of fluvoxamine and tadalafil sufficient to ensure constant levels of both the fluvoxamine and tadalafil compounds in the synaptic clefts of the patient's brainstem serotonergic pathways throughout the day.

4. The method of claim 3, wherein the therapeutically effective amount of the tadalafil is from 5 to 10 mg twice daily, and the therapeutically effective amount of the fluvoxamine is from 12.5 to 150 mg twice daily.

5. The method of claim 3, wherein the therapeutically effective amount of the tadalafil is the upper limit conventionally used to treat pulmonary hypertension, and the therapeutically effective amount of the fluvoxamine is the upper limit conventionally used to treat one of the disorders selected from the group consisting of depression, obsessive-compulsive disorder, and agoraphobia.

6. The method of claim 1 further comprising alternatingly titrating the amounts of the fluvoxamine and tadalafil over time to determine the therapeutically effective amounts.

7. The method of claim 1 further comprising monitoring the patient's blood chemistry prior to and during treatment for at least one of the following: liver function, kidney function and electrolyte level.

8. The method of claim 1 further comprising examining the physical state of the patient prior to treatment by conducting at least one of the tests selected from the following group: EKG and treadmill test.

* * * * *